United States Patent
Lee

[19]

[11] Patent Number: 6,066,170
[45] Date of Patent: *May 23, 2000

[54] METHOD AND APPARATUS FOR ADJUSTING CORNEAL CURVATURE

[75] Inventor: Joseph Y. Lee, Loma Linda, Calif.

[73] Assignee: MicroOptix LLC, Loma Linda, Calif.

[*] Notice: This patent is subject to a terminal disclaimer.

[21] Appl. No.: 09/045,283

[22] Filed: Mar. 20, 1998

Related U.S. Application Data

[63] Continuation of application No. 08/761,362, Dec. 9, 1996, Pat. No. 5,733,334.

[51] Int. Cl.$^7$ ........................................ A61F 2/14
[52] U.S. Cl. .................................................. 623/5
[58] Field of Search ............................ 623/4–5; 606/107, 606/166, 167

[56] References Cited

U.S. PATENT DOCUMENTS

| | | |
|---|---|---|
| 4,298,004 | 11/1981 | Schachar et al. . |
| 4,452,235 | 6/1984 | Reynolds . |
| 4,607,617 | 8/1986 | Choyce . |
| 4,624,669 | 11/1986 | Grendahl . |
| 4,655,774 | 4/1987 | Choyce . |
| 4,688,570 | 8/1987 | Kramer et al. . |
| 4,815,463 | 3/1989 | Hanna . |
| 4,834,750 | 5/1989 | Gupta . |
| 4,941,093 | 7/1990 | Marshall et al. . |
| 4,961,744 | 10/1990 | Kilmer et al. ........................ 606/166 |
| 4,976,719 | 12/1990 | Siepser . |

(List continued on next page.)

FOREIGN PATENT DOCUMENTS

| | | |
|---|---|---|
| 3 88 746 | 7/1973 | U.S.S.R. . |
| 94/03129 | 2/1994 | WIPO ...................................... 623/5 |
| WO 94/05232 | 3/1994 | WIPO . |
| WO 95/03755 | 2/1995 | WIPO . |
| WO 95/15719 | 6/1995 | WIPO . |

OTHER PUBLICATIONS

Burris, Terry E., et al., "Effects of Intrastromal Corneal Ring Size and Thickness on Corneal Flattening in Human Eye," *Refractive & Corneal Surgery*, vol. 7, Jan./Feb. 1991, pp. 46–50.

Burris, Terry E, et al., "Flattening of Central Corneal Curvature with Intrastromal Corneal Rings of Increasing Thickness: An Eye–Bank Study," *Journal of Cataract Refractive Surgery*, vol. 19, Supplement 1993, pp. 182–187.

Azar, Dimitri T., M.D., Editor, *Refractive Surgery*, pp. 1–2; Hjortdal, Jesper O., "Corneal Biomechanics in Refractive Surgery," Chap. 15, pp. 197–208; Verify, Steven M. et al, "The Instrastromal Corneal Ring for the Correction of Myopia," Chap. 27, pp. 365–372; Khoury, Johnny M. et al., "Intracorneal Alloplastic Inclusions," Chap. 28 pp. 373–384, Appleton & Lange, Stamford, Connecticut, copyright 1997.

Barraquer, Jose, "Basis of Refractive Keratoplasty—1967," *Refractive & Corneal Surgery*, vol. 5, pp. 179–193, May/Jun. 1989.

(List continued on next page.)

*Primary Examiner*—David H. Willse
*Attorney, Agent, or Firm*—McCutchen, Doyle, Brown & Enersen LLP

[57] ABSTRACT

A method and apparatus for adjusting corneal curvature of the eye comprising an adjustable split ring formed of an elastic hollow shell which is implantable into the cornea in encircling relation to the central optic zone of the cornea. The ring is filled by a predetermined amount with a select quantity of biocompatible material, either a fluid or strands of biocompatible suture material or polymethylmathacrylate, of predetermined size and length.

The biocompatible filler material is strategically located within the elastic shell to alter its dimensions in thickness or diameter and thereby adjust the corneal curvature to correct for refractive error. Further adjustment of the ring may be made post-operatively after implantation by select removal of the biocompatible filler material.

7 Claims, 12 Drawing Sheets

U.S. PATENT DOCUMENTS

| | | |
|---|---|---|
| 5,090,955 | 2/1992 | Simon . |
| 5,123,921 | 6/1992 | Werblin et al. . |
| 5,188,125 | 2/1993 | Kilmer et al. . |
| 5,236,970 | 8/1993 | Christ et al. . |
| 5,300,118 | 4/1994 | Silvestrini et al. ............ 623/5 |
| 5,312,424 | 5/1994 | Kilmer et al. . |
| 5,318,047 | 6/1994 | Davenport et al. . |
| 5,331,073 | 7/1994 | Weinschenk, III et al. . |
| 5,372,580 | 12/1994 | Simon et al. . |
| 5,391,201 | 2/1995 | Silvestrini et al. . |
| 5,466,260 | 11/1995 | Silvestrini et al. . |
| 5,480,950 | 1/1996 | Wang et al. . |
| 5,505,722 | 4/1996 | Kilmer et al. . |
| 5,547,468 | 8/1996 | Simon et al. . |
| 5,607,437 | 3/1997 | Simon et al. . |
| 5,693,092 | 12/1997 | Silvestrini et al. . |
| 5,733,334 | 3/1998 | Lee ............................ 623/5 |

OTHER PUBLICATIONS

Beekhuis, W. Houdjin, et al., "Complications of Hydrogel Intracorneal Lenses in Monkeys," *Arch Ophthalmol,* vol. 105, Jan. 1987, pp. 116–122.

Beekhuis, W. Houdjin, et al., "Hydration Stability of Intracorneal Hydrogel Implants," *Investigative Ophthalmology & Visual Science,* Nov. 1985, vol. 26, pp. 1634–1636.

Beekhuis, W. Houdjin, et al., "Hydrogel Keratophakia: A Microkeratone Dissection in the Monkey Model," *British Journal of Ophthalmology,* 1986, 70, 192–198.

Blavatskaia, D.E.D. "The Use of Intralamellar Homoplasty in Order to Reduce Refraction of the Eye," Department of Eye Diseases of the Yerevan Institute for Advancement of Physicians, pp. 1–7.

Climenhaga, Harold et al., "Effect of Diameter and Depth on the Response to Solid Polysulfone Intracorneal Lenses in Cats," *Arch Ophthalmol,* vol. 106, Jun. 1988, pp. 818–824.

Elander, Richard M.D., Editor, et al., *Principles and Practice of Refractive Surgery,* pp. 1–3; McCarey, Bernard E., "Alloplastic Materials in Lamellar Surgery," pp. 261–276; Thompson, Keith P. et al., "Synthetic Epikeratoplasty," Chap. 39, pp. 405–413; Schanzlin, David J. et al., "Intrastromal Corneal Ring," Chap. 40 pp. 415–419, W.B. Saunders Company, Philadelphia, Pennsylvania, copyright 1997.

Fleming, Joseph F., et al., "The Intrastromal Corneal Ring: Two Cases in Rabbits," *Journal of Refractive Surgery,* Nov./Dec. 1987; vol. 3, No. 6, pp. 227–232.

Harr, Dawn, Keravision Begins Implanting Corneal Reshaping Device in Blind Eyes, *Refract & Corneal Surgery,* 7:343 (Sep./Oct. 1991).

Hartmann, et al. "Kongreb der Deutschen Gesellschaft fur Intraokularlinsen Implantation," New York (with English translation "Intrastromal Implantation of an Adjustable Plastic Ring to Alter the Corneal Refraction," University Eye Clinic, Cologne, Germany).

Kuhne, F., et al., Abstract entitled: "Results of a 2–Year Animal Experiment with Reticulated Polyethylene Oxide Intrastromal Rings," *Journal of Fr. Ophthalmology,* vol. 17, 1994.2.

McCarey, Bernard E., Ph.D., et al., "Refractive Keratoplasty in Monkeys Using Intracorneal Lenses of Various Refractive Lenses," *Arch Ophthalmol,* vol. 105, Jan. 1987, pp. 123–126.

McCarey, Bernard E., Ph.D., et al., "Refractive Keratoplasty with intrastromal Hydrogel Lenticular Implants," *Investigative Ophthalmology Visual Science,* Jul. 1981, vol. 21, No. 1., Part 1, pp. 107–115, copyright 1981.

Simon, Gabriel, et al., "Gel Injection Adjustable Keratoplasty," *Graefe's Arch Clin Exp Opthalmol* (1991) 229:418–424, pp. 418–424.

Simon, Gabriel, et al., "Modification, Calibration, and Comparative Testing of an Automated Surgical Keratomerter," *Refractive & Corneal Surgery,* vol. 7, pp. 151–160, Mar./Apr. 1991.

Simon, Gabriel, et al., "Refractive Modeling of the Corneal by Intrastromal Rings," Instituto Barraquer, Barcelona, Spain and Bascom Palmer Eye Institute, University of Miami, Florida, Department of Opththalmology.

Simon, Gabriel, et al., "Refractive Modeling of the Corneal by Intrastromal Rings," Association of Research in Vision and Ophthalmology Annual Spring Meeting, Sarasota, Florida, Apr. 30–May 5, 1989, p. 187.

Thompson, Keith P., et al., "Emerging Techologies for Refractive Surgery: Laser Adjustable Synthetic Epikeratoplasty," *Refractive & Corneal Surgery,* vol. 5, pp. 46–48, Jan./Feb. 1989.

Thompson, Keith P., et al., "Will the Excimer Laser Resolve the Unsolved Problems with Refractive Surgery?" *Refractive & Corneal Surgery,* vol. 6, pp. 315–317, Sep./Oct. 1990.

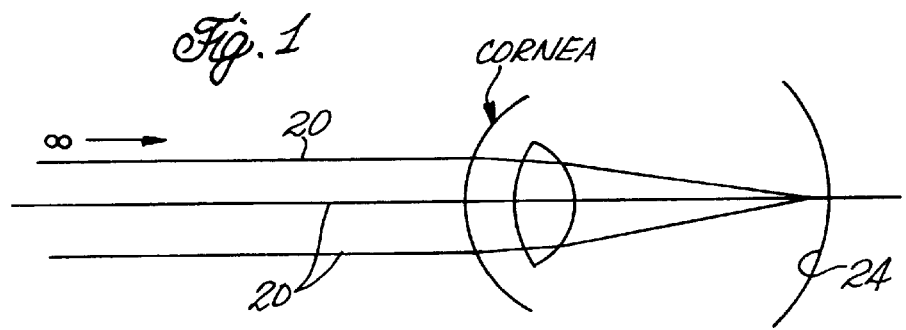
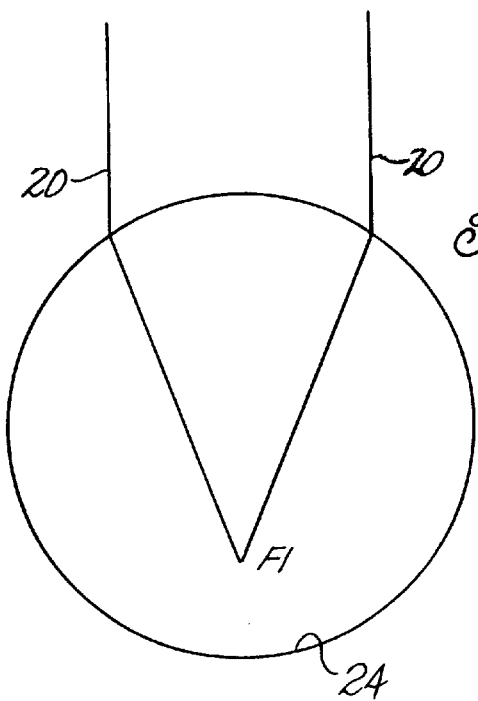
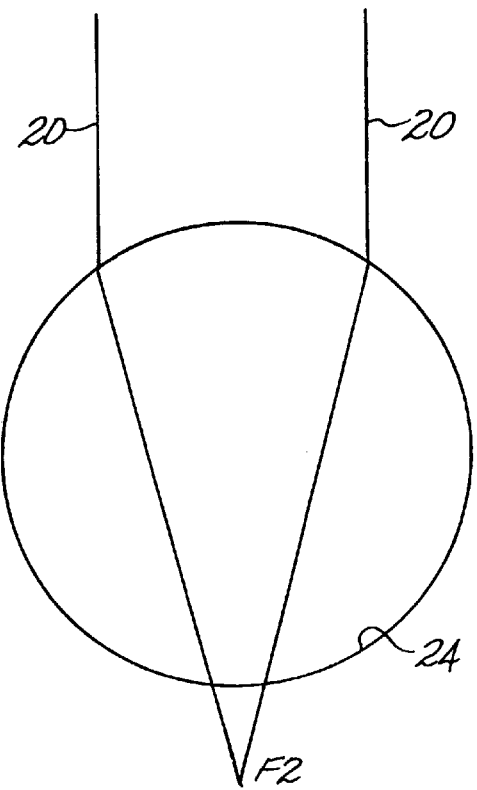

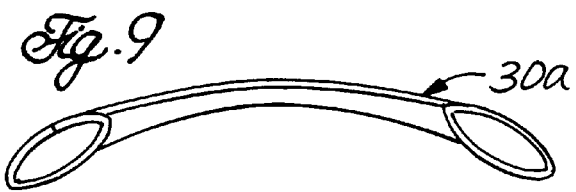
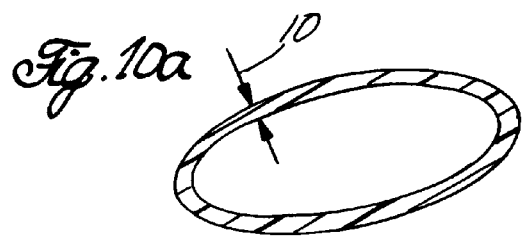
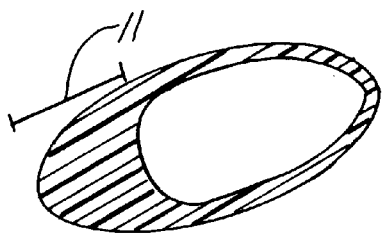
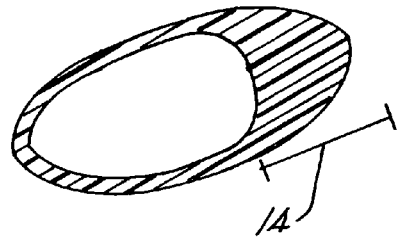
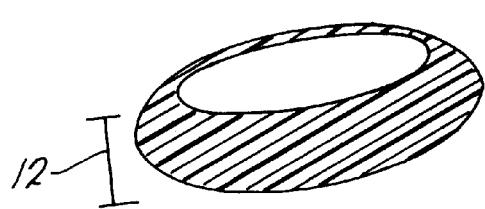

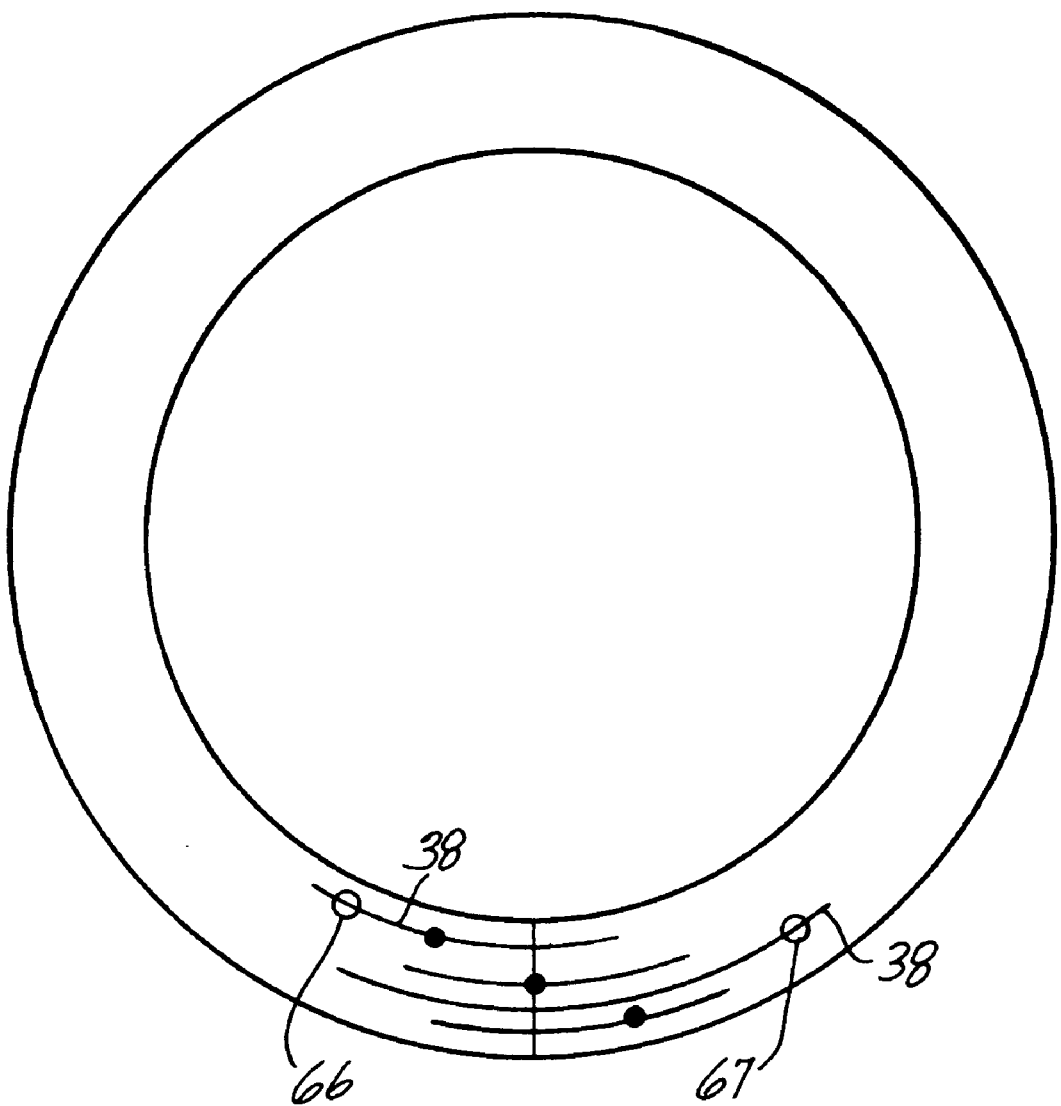

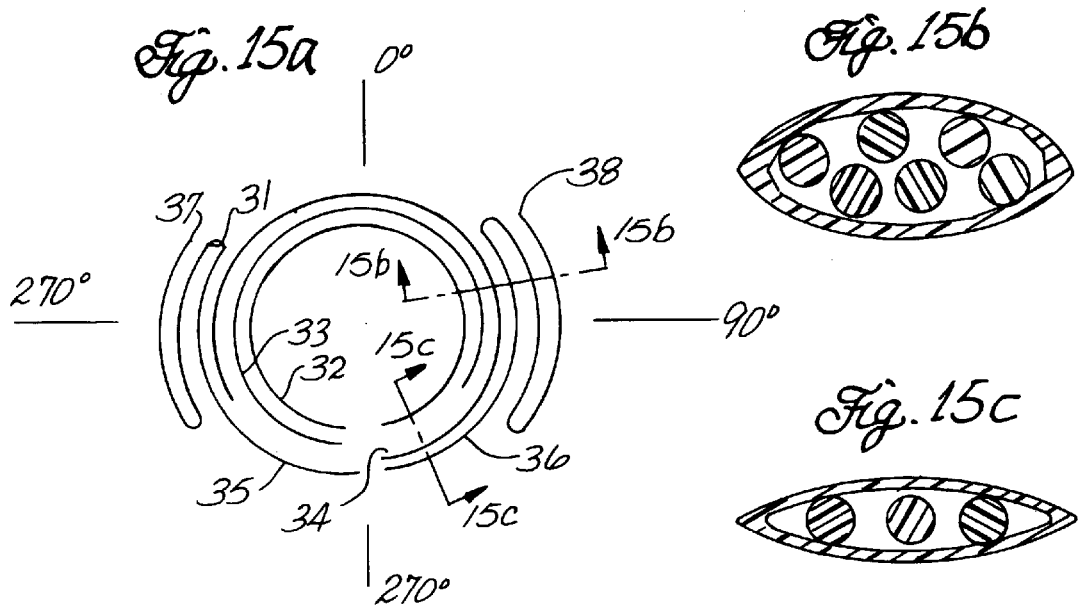
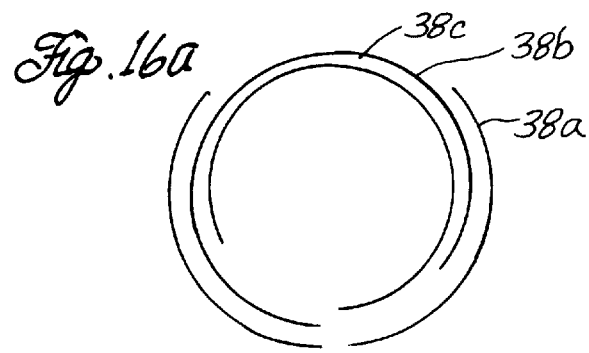
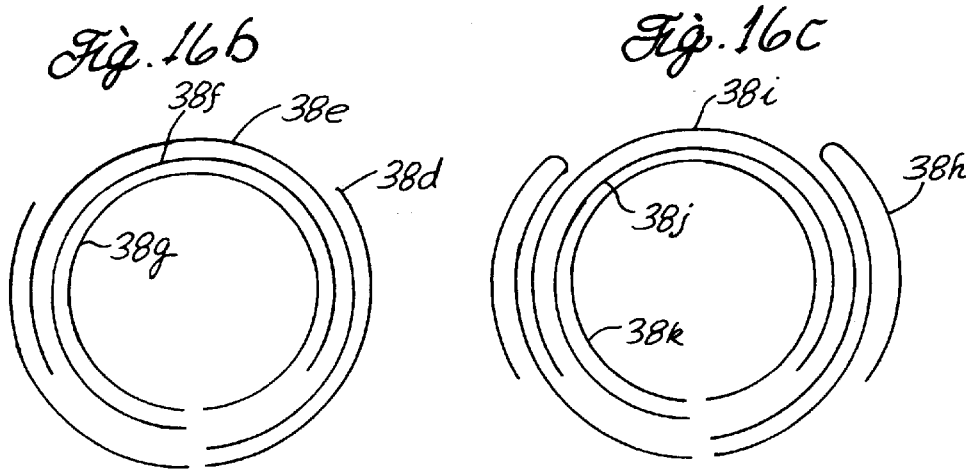

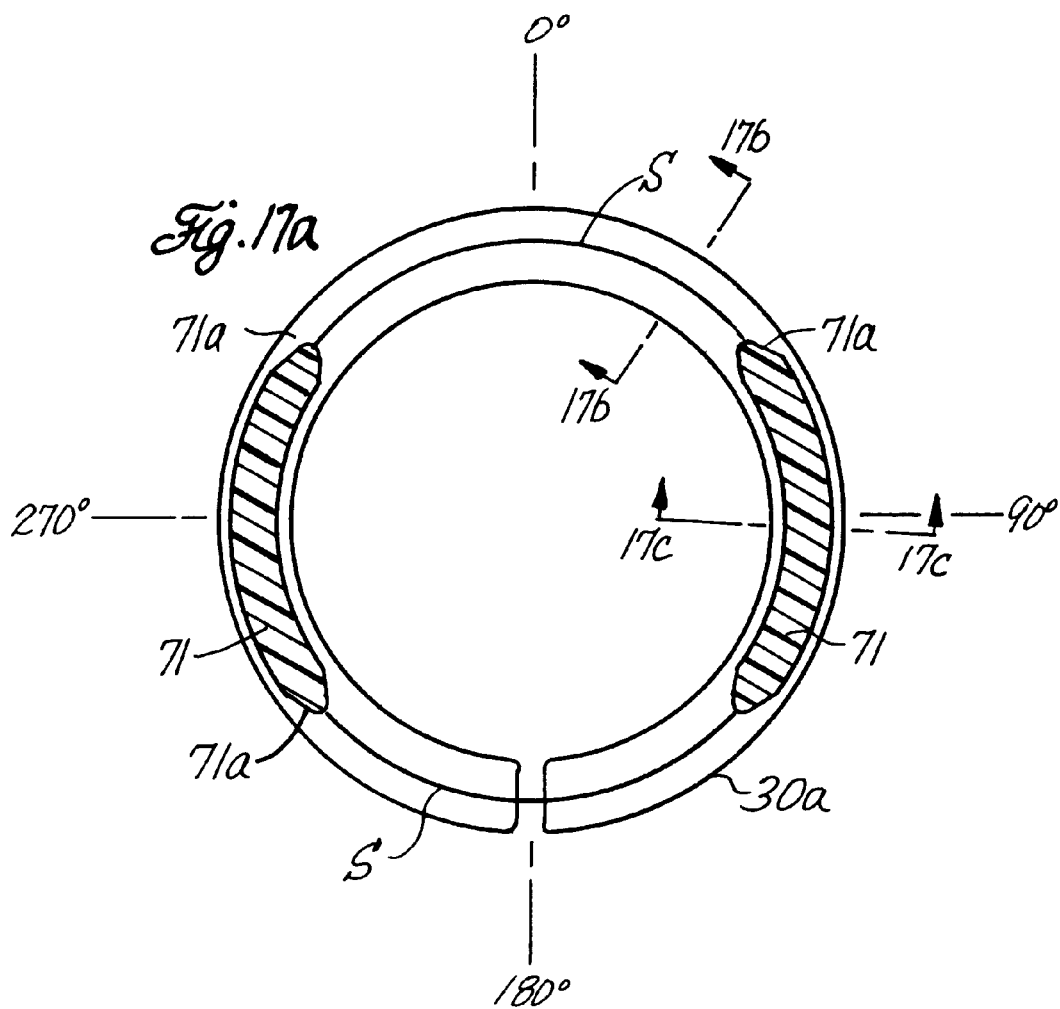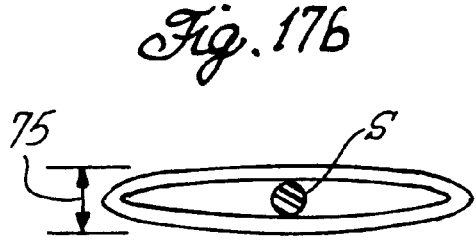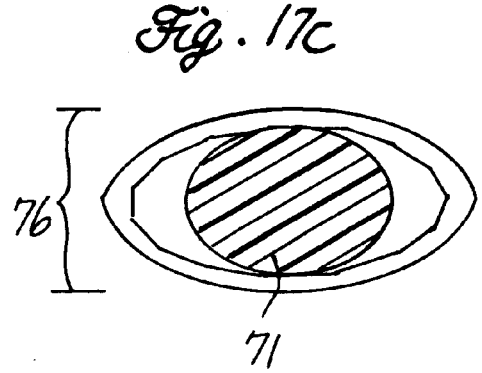

METHOD AND APPARATUS FOR ADJUSTING CORNEAL CURVATURE

RELATED U.S. APPLICATIONS

This application is a continuation of Application Ser. No. 08/761,362, filed Dec. 9, 1996, now U.S. Pat. No. 5,733,334.

FIELD OF THE INVENTION

This invention relates to a method and apparatus for adjusting corneal curvature and, more particularly, to an implantable ring adapted for insertion into the cornea of an eye and which may be adjusted in thickness and diameter at the time of insertion and at post-operative times to correct refractive error.

BACKGROUND OF THE INVENTION

Ametropia, an undesirable refractive condition of the eye, has three main subdivisions: myopia, hyperopia, and astigmatism. In myopia, by far the most common type of ametropia, the parallel light rays 20 which enter the eye as shown in FIG. 1 come to a focus F1 in front of the retina 24 as shown in FIG. 2. In hyperopia, the rays of light 20 come to a focus F2 behind the retina 24 as shown in FIG. 3. When the rays of light converge to not one, but several foci, it is referred to as astigmatism, in which condition the various foci may all lie before the retina; all lie behind the retina; or partly before and partly behind the retina.

Ametropia is usually corrected by glasses or contact lenses. However, these refractive disorders may also be corrected by surgery. Refractive eye surgery is defined as that surgery on the eye which acts to change the lightbending qualities of the eye. More common current refractive procedures include radial keratotomy, as described in U.S. Pat. Nos. 4,815,463 and 4,688,570 and also laser ablation of corneal stroma, described in U.S. Pat. No. 4,941,093. Various other surgical methods for the correction of refractive disorders have been tried including thermokeratoplasty for the treatment of hyperopia, epikeratoplasty to correct severe hyperopia, and keratomileusis which can steepen or flatten the central cornea. Keratomileusis was introduced by Barraquer of Colombia in 1961 and essentially involves grinding a corneal button into an appropriate shape to correct the refractive error and replacing the reshaped corneal button. Some of the more common keratorefractive procedures are discussed below, none of which have currently shown itself to have all the characteristics of an ideal keratorefractive procedure.

In radial keratotomy (RK) multiple peripheral radially directed incisions are made into the cornea at 90–95% depth in an attempt to flatten the central cornea and thus correct myopia. The problem of unpredictability of result was tackled by multiple extensive retrospective analyses of the patients in whom surgery had already been performed. These studies revealed certain factors that seemed to control the outcome of the surgery, such as the size of the optical zone, the initial keratometric readings, corneal diameter, corneal rigidity, number of incisions, incisional depth, intraocular pressure, thickness of the cornea, and degree of astigmatism. Age and sex are also factors that are taken into consideration in most of the nomograms which have been devised to predict what effect to expect for a certain surgery. At one point, many experts in the field considered it nearly impossible to fully and accurately correct patients in one surgery and felt that RK should be considered a two-stage surgery, with the initial surgery to achieve the "ball-park" correction, followed by an enhancement procedure to fine-tune the original correction. It was felt that because of individual variability which may lead to an under or over-correction in the individual different from that predicted by the nomogram, attempting to fully correct the refractive error in one surgery could lead to over-correction in a not insignificant percent of the surgeries, resulting in hyperopia which is much more difficult to correct. Unfortunately, the second-stage surgery is even less predictable than the initial procedure. No one has yet devised a formula to take into account the profound changes which occur in the cornea after the initial RK, especially when weeks or months have passed. It is obvious that RK does not qualify as a simple, safe, predictable procedure to adjust the refractive outcome after the initial RK has been performed. Most ideas to contend with the corneal shape after this event have been purely empiric. Thus an easy method to fine-tune a refractive correction that is minimally invasive and easily performed, would require serious consideration.

Laser stromal ablation procedures, such as photorefractive keratectomy (PRK) for correction of refractive disorders are currently popular and have had reasonable success. These procedures are not, however, spared from the problem of unpredictability. Essentially, in the treatment of myopia, laser energy is imparted to the central cornea thereby causing excision of more tissue centrally and a resultant flattening of the cornea. Unfortunately, the final refractive effect is determined not only by the amount of ablation but also by the healing response to the keratectomy. The cornea actively lays down new collagen and the epithelium undergoes a hyperplastic response, among other responses, in an attempt to repair the damage to its surface. This causes regression, or a shift backwards towards myopia, which can gradually occur over a period of months to years. An undesired effect of new collagen deposition is stromal scar formation which manifests as stromal haze and possible decrease in contrast sensitivity by the patient. Predictability with PRK is an issue, as with RK. Most published results of outcome after PRK treatment for myopia show 80–94% of eyes obtaining uncorrected visual acuity of 20/40 or better while the percentage of patients achieving 20/20 is significantly less. Although visual recovery is slow in RK, it is quicker than after PRK. A second laser ablation procedure is usually undertaken with caution since it may cause a greater healing response with even more regression than the initial procedure. Again, as in RK, the laser ablation procedure is not completely predictable, partly because one cannot predict an individual's wound healing response.

For years it has been thought that refractive surgery with intracorneal implants could be used in the correction of ametropia. Early techniques included lamellar removal or addition of natural corneal stromal tissue, as in keratomileusis and keratophakia. These required the use of a microkeratome to remove a portion of the cornea followed by lathing of either the patient's (keratomileusis) or donor's (keratophakia) removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predictable fashion. The use of alloplastic intracorneal lenses to correct the refractive state of the eye, first proposed in 1949 by Jose Barraquer, have been plagued with problems of biocompatibility, permeability to nutrients and oxygen, corneal and lens hydration status, etc. Other problems with these lenses included surgical manipulation of the central visual axis with the concomitant possibility of interface scarring.

More recent efforts toward the correction of refractive errors have focused on minimizing the effects of the wound healing response by avoiding the central cornea. There have been multiple attempts to alter the central corneal curvature by surgically manipulating the peripheral cornea. These techniques are discussed because of their specific relevance to this invention. The general concept of making fixed changes in the corneal curvature was adapted by A. E. Reynolds in a unique way (U.S. Pat. No. 4,452,235). He describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the dissecting member, reversibly moving the dissecting member about the path, and thereby pulling the adjusting member about the circular path, made by the dissecting member, withdrawing the dissecting member, adjusting the ends of the split ring shaped adjusting member relative to one another to thereby adjust the ring diameter to change the diameter and shape of the cornea and fixedly attaching the ring's ends by gluing to maintain the desired topographical shape of the cornea.

A major advantage of this ring was that a very minimal wound healing effect was expected. A marked corneal wound healing response would decrease the long-term stability of any surgical refractive procedure. However, there are two distinct problem areas affecting the refractive outcome of surgical procedures treating ametropia.

1. The first area involves the ability to predetermine the shape and size of a ring that will lead to a certain refractive outcome. In RK or PRK, retrospective studies have been performed that led to the development of nomograms which predict that a certain depth cut or a certain ablation amount will result in a predictable amount of correction. In the case of the ring, eventually nomograms will be developed that can be used to predict a given refractive correction for a given thickness or size of the ring. However, these nomograms can never fully account for individual variability in the response to a given keratorefractive procedure.

2. The refractive outcome also depends on the stability of the refractive correction achieved after surgery. To reiterate, the advantage of the ring would be the stability of the refractive outcome achieved because of a presumed minimal wound healing response. This decreases the variability of the long-term refractive outcome but still does not address the problems posed in the first problem area, —the inherent individual variability, in that while the outcome may be stable, it may very well be an inadequate refractive outcome that is stable.

Another unaddressed issue is that even with the ring, surgeons will aim for a slight undercorrection of myopia because, in general, patients are more unhappy with an overcorrection that results in hyperopia. Again, the refractive outcome may be more stable than in RK or PRK but it may be an insufficient refractive result that is stable.

Simon in U.S. Pat. No. 5,090,955 describes a surgical technique that allows for modification of the corneal curvature by interlamellar injection of a synthetic gel at the corneal periphery while sparing the optical zone. He does discuss an intra-operative removal of gel to adjust the final curvature of the central corneal region, but it has yet to be shown that the gel injection keratoplasty results in a stable refractive outcome. Also, a post-operative adjustment is not disclosed, but it would be difficult at best with such a technique.

Siepser (U.S. Pat. No. 4,976,719) describes another ring-type device to either flatten or steepen the curvature of the cornea by using a retainer ring composed of a single surgical wire creating a ring of forces which are selectively adjustable to thereby permit selective change of the curvature of the cornea, —the adjustable means comprising a turnbuckle attached to the wire.

Silvestrini et al. in U.S. Pat. No. 5,466,260 describes an adjustable intrastromal corneal ring (ICR) but states that the essence of the invention lies in the ability of the ring to be adjusted in thickness so that it is not necessary to stock a plurality of different rings of different sizes. It becomes obvious that the rings are not designed to be adjusted within the cornea at a later post-operative date. Silvestrini et al further states that "it may not be further adjustable after insertion." The idea of an inflatable ring implant was raised by Silvestrini as a way to decrease the number of different size rings that would need to be stocked, but he does not mention the idea of an inflatable ring that could be adjusted following surgery.

There are several mechanisms by which peripheral manipulation of the cornea affects anterior corneal curvature. The cornea, like most soft tissues, is nonlinear, viscoelastic, nonhomogeneous, and can exhibit large strains under physiologic conditions. The whole eye is geometrically extremely complex and the biomechanics technique capable of systematically modeling this reality is the finite element method which assumes small strains (a measure of deformity), homogeneity, and linear elastic behavior. Two simple mechanisms will be briefly described.

A simple example is helpful in understanding the first mechanism. Assume a loose rope R between two fixed points P1 and P2 as in FIG. 4a, which forms a curve, the lowest point P being in the middle. Referring to FIG. 4b, a weight W placed on the rope between the middle point P and one fixed point will cause the central portion of the rope to straighten. The cornea C demonstrated in FIG. 5(a) and FIG. 5(b) behaves similarly, the two fixed points, P1 and P2, analogous to the limbus of the eye and the weight W similar to the intrastromal ring 30 which, when inserted in the cornea in surrounding relation to the cornea's central optical zone, causes the corneal collagen fibers to deviate upwards at (21) above the ring, and downwards at (22) below the ring. In essence, this deviation of the cornea around the peripheral ring causes other areas of the cornea to lose "slack", or relatively straighten as shown at (23).

Mechanical expansion of the ring diameter as shown by expansion of the ring 30 in FIG. 6(b) as compared to FIG. 6(a) also flattens the central corneal curvature whereas constriction of the ring 30 steepens the central corneal curvature, analogous to the two fixed points in the example, FIG. 4(a) and FIG. 4(b), being moved together and causing the rope in the middle to sag more. This is permitted to occur, in part, because the boundary nodes at the limbus are not completely fixed. In summary, there is a microdeviation caused by the bulk of the ring 30 itself within the peripheral tissue, slightly flattening the central curvature of the cornea, and a constricting or expanding ring altering the fixed points and thus altering corneal curvature. A constricting or expanding ring is likely to cause a less stable refractive outcome because the inward or outward forces of the ring against the corneal stroma may gradually cause further lamellar dissection and dissipation of the forces. A more consistent outcome is likely to be achieved with varying the thickness of the ring itself.

The second mechanism is aptly described by J. Barraquer in the following quote. Since 1964, "It has been demonstrated that to correct myopia, thickness must be subtracted from the center of the cornea or increased in its periphery, and that to correct hyperopia, thickness must be added to the center of the cornea or subtracted from its periphery." Procedures involving subtraction were called "keratomileusis" and those involving addition received the name of "keratophakia". Intrastromal corneal rings add bulk to the periphery and increasing the thickness of the ring results in a more pronounced effect on flattening of the anterior corneal curvature.

The ideal keratorefractive procedure allows all the advantages of eyeglasses or contact lenses, namely, being able to correct a wide range of refractive errors, accuracy or predictability, allowing reversibility in the event that the refractive state of the eye changes and it becomes necessary to adjust the correction again, yielding minimal complications, and associated with technical simplicity, low cost, and being aesthetically acceptable to the patient.

Once again, an easy procedure to post-operatively fine-tune the refractive correction and corneal curvature which is often influenced by changes in corneal hydration status, wound healing responses, and other unknown factors, is not available. In this disclosure of the present invention, an easy method to adjust the refractive outcome after the corneal curvature has stabilized, a method that is minimally invasive, a method causing minimal stimulation of the wound healing processes, allowing repetitive adjustments as deemed necessary, and being almost completely reversible is described. It may make moot the pervasive issue of unpredictability and make obsolete the application of procedures which rely heavily upon nomograms to predict refractive outcome and are thus unable to adequately account for an individual's variable response to the procedure.

SUMMARY OF THE INVENTION

The present invention concerns the use of an adjustable intrastromal ring adapted for implantation in the cornea and formed of an elastic hollow shell composed of a material such as a silicone or urethane polymer, with an annular chamber that may be filled with a biocompatible material such as saline silicon gel, polymethylmethacrylate (PMMA), or a variable number of permanent suture strands of variable size in thickness and length to augment the thickness of the ring. The ring is first split by a radial cut, filled with a predetermined amount of the biocompatible material, and implanted in the cornea in surrounding relation to the optical zone of the cornea. The corneal curvature is then adjusted by either cutting one or more suture strands placed at variable tensions, to relieve constricting radial forces and thereby decreasing corneal curvature, or by complete removal of one or more suture strands thus decreasing the thickness of the ring and in steepening the corneal curvature and producing a myopic shift. These relatively simple adjustments for refractive correction can be performed with surgical instruments commonly available and require minimal post-operative manipulation of the cornea and the implanted adjustable ring.

The apparatus of the invention is an adjustable hollow ring which is adjustable in thickness and diameter and adapted to be inserted into the interlamellar space of the corneal stroma for the purpose of correcting refractive error. The ring is easily adjustable on multiple occasions following the initial surgery of implantation and thus allows for adjustment of the refractive outcome at a later date without necessitating the removal of the implanted ring.

BRIEF DESCRIPTION OF THE DRAWINGS

FIG. 1 is a schematic representation of a horizontal section of the human eye;

FIG. 2 is a schematic representation showing how the light rays focus in front of the retina of the eye in the condition of myopia;

FIG. 3 is a schematic representation showing how light rays focus behind the retina of the eye in the condition of hyperopia;

FIG. 9 is a perspective diametral section view of the ring of the invention, showing the angle of the conic shaped radial cross sections;

FIGS. 10(a)–10(d) are radial cross section views of modified forms of the ring of the invention;

FIG. 11 is a plan view of the ring showing possible suture knot placement in the strands of suture material placed inside the ring;

FIG. 15(a) is a schematic plan view of the orientation and form of a plurality of strands of suture material which may be inserted into the interior of the ring; the spacing therebetween exaggerated for purpose of illustration;

FIGS. 15(b) and 15(c) are cross sections of the ring of the invention as taken along the section lines b—b and c—c in FIG. 15(a), respectively;

FIGS. 16(a), 16(b), and 16(c) show variations in the configuration and orientation of strands of suture material which are suitable for insertion in the ring;

FIG. 17(a) is a schematic showing a plan view of a ring of the invention wherein curved rods have been inserted in the ring;

FIG. 17(b) is a view in radial cross section of the ring in FIG. 17(a) as taken along the section line 17b—17b;

FIG. 17(c) is a view in radial cross section of the ring in FIG. 17(a) as taken along the section line 17c–17c;

DETAILED DESCRIPTION OF THE INVENTION

Figure 4A:
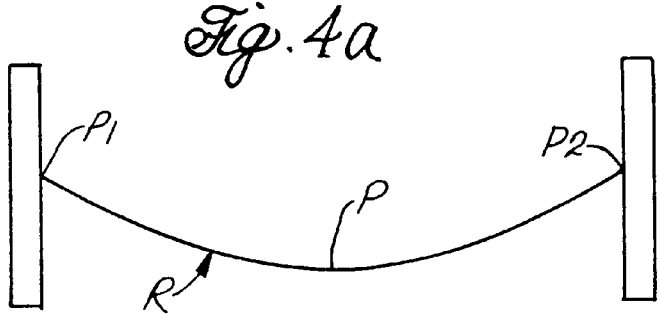
FIG. 4(a) is a schematic illustration for showing a rope suspended at its ends between two fixed points.
Figure 4B:
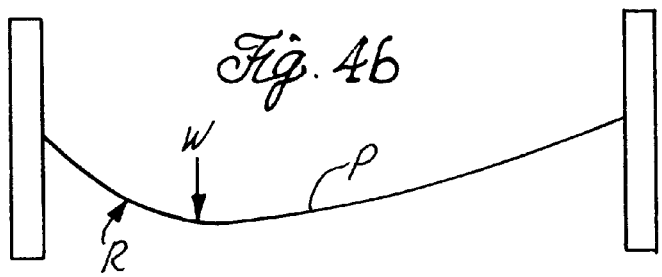
FIG. 4(b) is a schematic illustration which shows the rope in FIG. 4(a) with the force of a weight applied to the rope between its midpoint and one of the fixed points.
Figure 5A:
FIG. 5(a) is a schematic illustration showing the cornea of an eye wherein the cornea is fixedly attached at diametrically opposed points on the surrounding limbus.
Figure 5B:
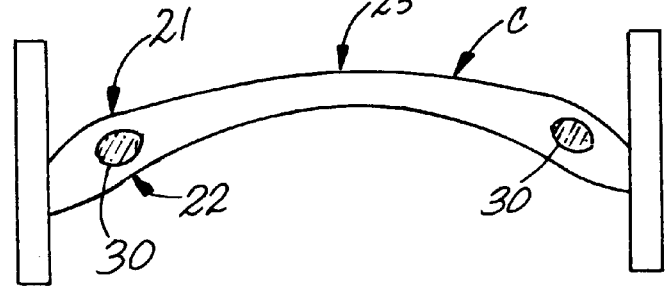
FIG. 5(b) is an illustration similar to FIG. 5(a) but showing the curvature effects produced on the cornea because of the presence of an intrastromal support ring in the cornea.
Figure 6A:
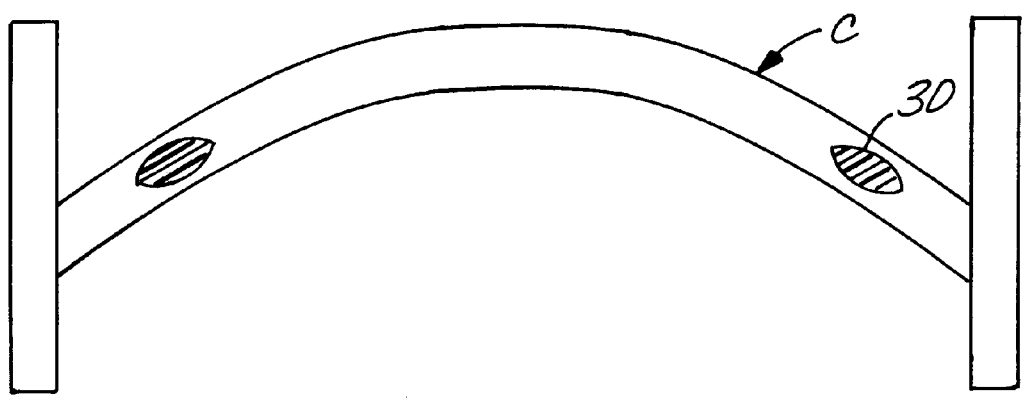
FIGS. 6(a) and 6(b) are cross sectional schematic views of a cornea for showing the effect produced by an expansion of the adjustable ring of the invention after its implantation in the cornea.
Figure 6B:
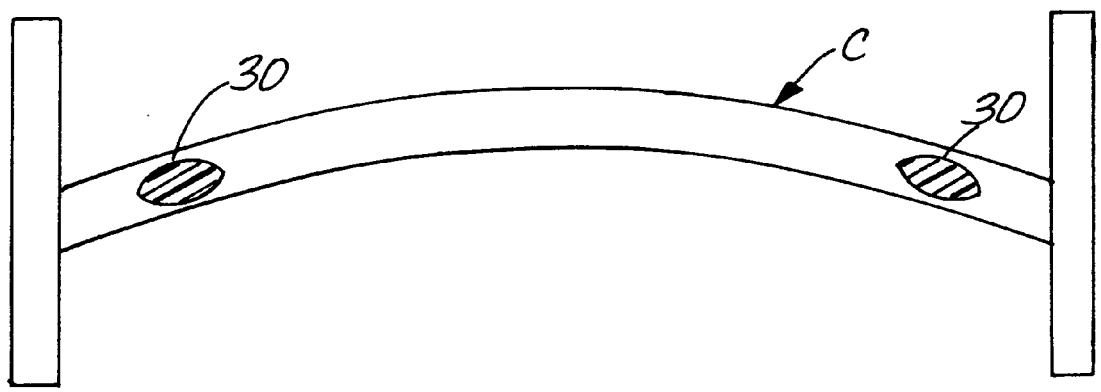
Figure 7A:
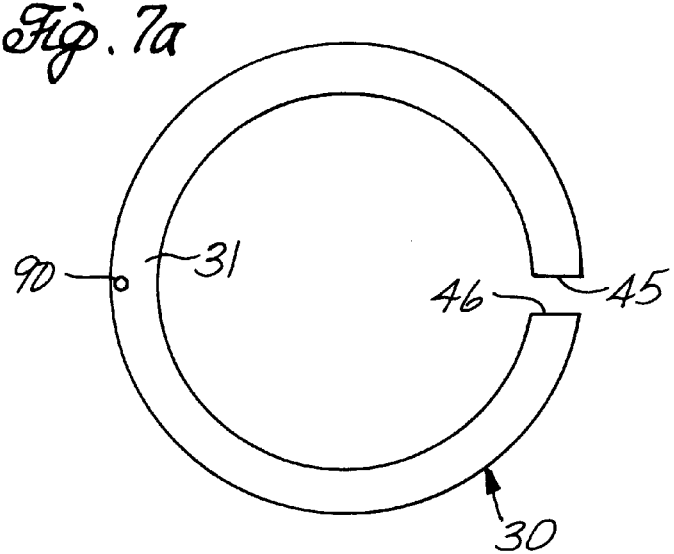
FIG. 7(a) is a plan view of the elastic ring of the invention wherein the ring has been severed by a radial cut.

Referring more particularly to the drawings, there is shown in FIG. 7(a) the apparatus of the invention which comprises an adjustable ring implant 30. The ring 30 forms an enclosure for receiving a filler which is easily removable, such as a biocompatible fluid, gel, PMMA filament or permanent surgical suture material such as nylon, polypropylene, mersilene, Dacron, stainless steel wire, silver, or tantalum. The ring 30 comprises a tubular shell 30a made of an elastic material, such as a silicone or urethane polymer and in FIG. 7(a) is shown as a split ring, having been split in preparation for its use in practicing the method of the invention. The shell material has adequate stiffness such that the ring will maintain its generally circular shape in plan view when sufficiently filled and also have adequate resiliency to allow an increase in thickness with filling as shown in the cross section view of FIG. 8(b) and flattening with removal of the filler material as shown in FIG. 8(c). The shell must have sufficient structural integrity, strength, elasticity and elongation ability to generally maintain its circular shape and be expandable. Its composition material may be similar to that used in producing foldable or deformable intraocular lenses such as a silicone polymer or that material used in soft contact lenses.

Figure 7B:
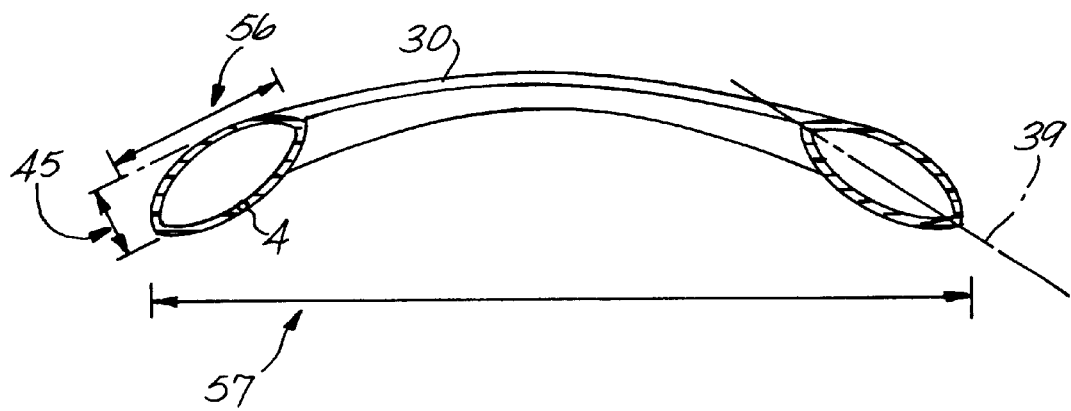
FIG. 7(b) is an enlarged diametral cross section view as taken along the section line 7b—7b in FIG. 7(a)
Figure 8A:
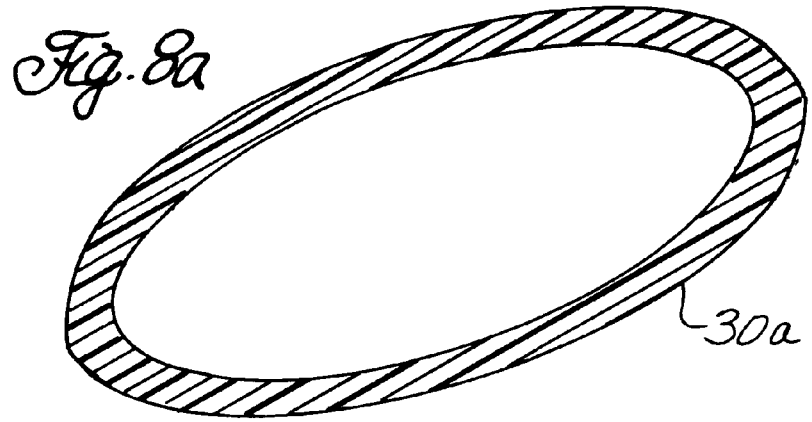
FIG. 8(a) is a perspective view of a ring of the invention.
Figure 8B:
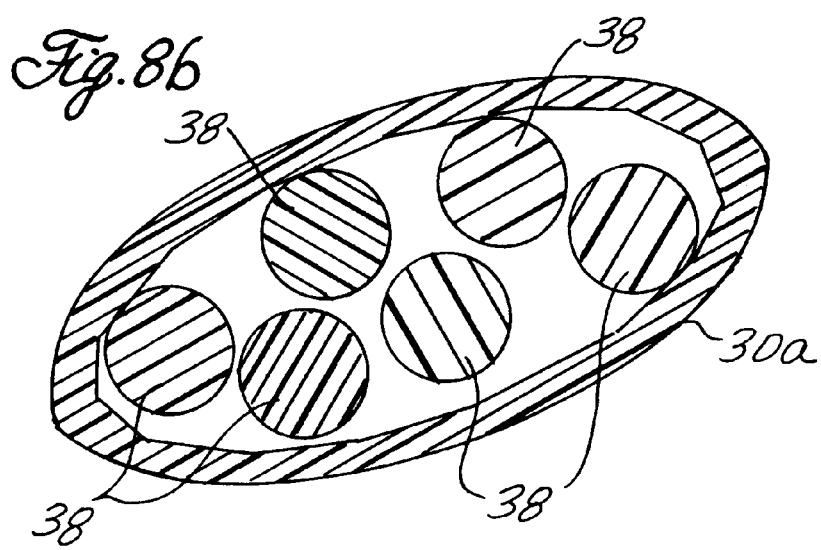
FIG. 8(b) is an enlarged radial cross section view of the tubular ring of the invention wherein the interior of the ring has been filled with a number of suture strands.
Figure 8C:
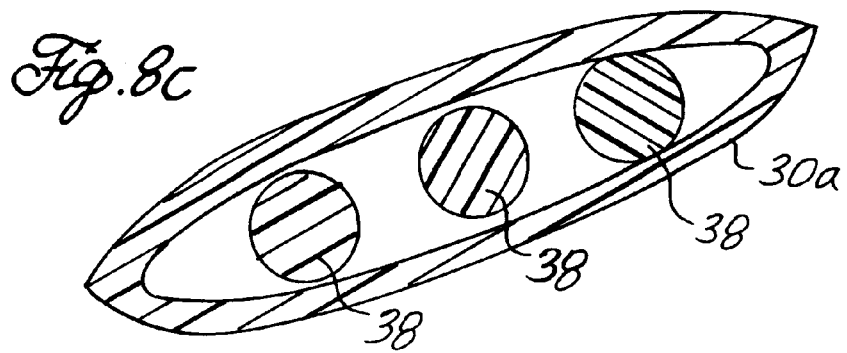
FIG. 8(c) is a cross section similar to FIG. 8(b) but wherein some of the strands of suture shown in FIG. 8(b) have been removed from the ring.

The cross section of the ring 30 as taken in a radial plane through the center of the ring is elliptically shaped as seen in the section views demonstrated in FIG. 8(a) and in FIG. 9. The different embodiments shown in FIGS.10(a)–10(d) can each be modified to provide a number of subembodiments by altering variables such as the composition material, manner of ring connection, cross-sectional surface parameters of the ring, e.g., forming the ring from cross sections in the form of a circle, square, rectangle, triangle, oval, etc. The major axis 39 of a transverse cross section of the ring 30 is such that it corresponds to the slope of the corneal arc of the anterior pole of the cornea, thus forming the conic section. This angle is approximately 20 to 25 degrees as shown in FIG. 7(b). The two ends 45,46 of the split ring are squared off so that they may juxtapose each other as shown in FIG. 7(a) and may be fixably joined at the time of surgery by such methods as suturing or gluing.

The ring 30 is adapted to be implanted into the peripheral stromal cornea. It is of a thickness and geometry such that when implanted it alters the central corneal curvature without intruding into the central optical zone of the cornea and without decreasing the diffusion of nutrients to the central cornea. It is of a size such that it can be readily inserted into the peripheral human cornea intrastromally and consists of an elastic material which is biocompatible, and more specifically, compatible with ocular issues. The dimensions as shown in FIG. 7(b) include a maximal thickness (55) (after complete augmentation) of 0.2–01.5 mm, width (56) of 0.5 to 1.5 mm and an outer over-all diameter (57) of 6.00 to 11.0 mm. The thickness of the shell 30(a) of this ring 30 may be varied as shown in FIGS. 10(a)–10(d). The ring may contain only one or multiple strands 38 of suture material of varying diameter and composition. The strands 38 may be composed of a permanent biocompatible material as used in ophthalmic surgery such as nylon, mersilene, polypropylene, stainless steel wire, silver, or tantalum. The size of the suture strand can vary from 10-0 to 2-0. It may be clear or colored. It may be marked towards the head and tail end of the ring to aid the surgeon in adjusting the tension when tying the sutures. The suture strand may have a pre-fabricated loop 66, 67 at one end as shown in FIG. 11 which would facilitate removal of the suture strand by using an instrument having a small hook at the operative end with which the loop can be snared. The loop also aids in preventing surrounding suture strands from being pulled out simultaneously by providing resistance at the open end. The suture is not necessarily tied.

The ring of the invention is designed to be implanted in the cornea of the eye to alter the external curvature of the central optic zone of the cornea without encroachment into the optic zone. It is comprised of a hollow ring of a thickness and circumference both of which are variable such that the central optic zone is flattened by suture strand cutting or lysis (expansion) or steepened in curvature by suture removal to an amount suitable to provide the refractive correction needed and allowing for adjustment of overcorrection or undercorrection of the refractive error.

Depending on the amount of refractive error, an appropriate embodiment varied in shape, size, circumference, suture size and variability, number of sutures present are chosen. The elastic shell 30a containing the suture material can also be varied as shown by the embodiments of ring illustrated in FIGS. 10(a)–10(d). The choices include:

1. The absence of a supporting polymethylmethacrylate (PMMA) ring. Suture strand tightening maximally affects the inner circumference in this ring. Suture cutting will have the most effect with this design if the sutures are initially tightened.

2. PMMA or other stiff physiologically acceptable polymer backbone reenforcing the inner circumference of the ring wall as shown in FIG. 10(c). The thickened areas 64 shown in FIG. 10(c) may be increased thickness of the elastic material composing the walls or it may be the stiff polymer backbone mentioned above. Suture tightening or lysis would have less effect on corneal curvature with this embodiment. During surgery, the inner circumference backbone could be appropriately adjusted and fixed with suture or glue, with gross adjustments aided by the use of a keratometer.

3. PMMA or other stiff polymer backbone reenforcing the outer circumference of the ring wall as shown in FIG. 10(b). In this situation, tightening the sutures increases central curvature and decreases ring thickness, both factors which effect a steepening of the cornea.

4. Support of both inner and outer circumferences.

The size of the ring chosen should be such that the range of overcorrection or undercorrection secondary to individual variability of response to surgery may be comfortably corrected (not requiring excessive tightening of the sutures or removal of all sutures) by the methods described. The maximal thickness, circumference, and type of supporting backbone is chosen prior to insertion of the ring. The ideal embodiment, given the preoperative refractive state and other pertinent data, is chosen prior to operating and then that embodiment further manipulated as necessary to determine the ideal curvature. The ring is inserted into the peripheral cornea at an adequate depth and then further adjusted by modifying the relative tightness of the sutures in order to more precisely adjust the shape of the cornea and focus the light entering the eye on the retina. The intraoperative keratoscope or automatic keratometer may be helpful in determining the tightness of the sutures.

The suture-filled ring can be implanted into the stroma of the peripheral cornea by the methods which have been shown in the past to be suitable for installation (U.S. Pat. application Ser. No. 07/867,745, CORNEAL VACUUM CENTERING GUIDE AND DISSECTOR and U.S. Pat. No. 5,466,260, ADJUSTABLE DEVICES FOR CORNEAL CURVATURE ADJUSTMENT). The ring is implanted into a circular lamellar channel formed at ½ to ⅔ corneal depth with a circular dissecting instrument that requires only a small midperipheral corneal incision. A knife is used to make an approximately 2 mm radial incision beginning at 2.5 to 3.5 mm from the corneal center. The surface of the cornea is cut only at this incision. A Suarez spreader is introduced into the bottom of the incision and a small lamellar channel created. Application of a vacuum centering guide is used to fix the globe while an 8–9 mm outer diameter Lamellar channeling tool introduced through the incision into the lamellar channel is rotated to produce a 360 degree channel around the corneal midperiphery at ½ to ⅔ corneal depth. After the channeling blade has been completely inserted, the elastic ring is attached to the head of the blade so that as the blade is withdrawn, the ring is progressively pulled into place. The head and tail are brought together and fixed. The elastic wall from the tail may cover the head, leaving no suture exposed to stroma, the suture knots of strands which are knotted may be left exposed to the stromal tissue, or the knots may be rotated under the shell in either direction as shown in FIG. 11. However, not all the sutures are necessarily tied.

In summary, adjustment or choice of ring size, shape, width, shell thickness, and circumference, factors affecting the corneal curvature and refractive outcome, occurs in three distinct temporal stages:

1. Preoperatively, the above mentioned variables and presence or absence of a supporting backbone are chosen using nomograms developed from retrospective is studies as a guide to the selection of each variable.

2. Intraoperatively, the ring tightness is adjusted as necessary, aided by the use of the intraoperative keratoscope if necessary. The suture strands passing completely around the ring are tightened and tied at various tensions, keeping the following in mind:

a. Adjusting the thickness of the ring probably results in a more predictable change in corneal curvature than attempting to adjust corneal curvature by either the application of tension to the circular suture or the removal of tension by lysing the suture.

b. If a hyperopic correction is required, circular radial forces will be necessary to maintain the corneal curvature and a larger suture strand is a better choice to maintain the corneal curvature with the appropriate tension.

Figure 12A:
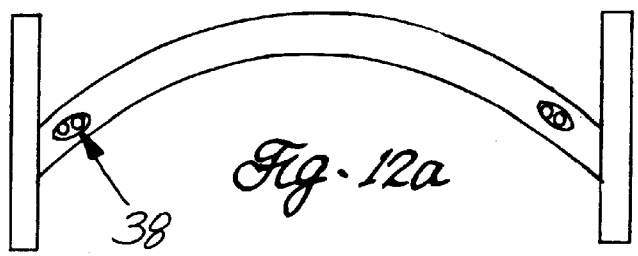
FIGS. 12(a) and 12(b) show cross-sectional views of the cornea and ring before and after strands of suture material placed inside the ring are cut.
Figure 12B:
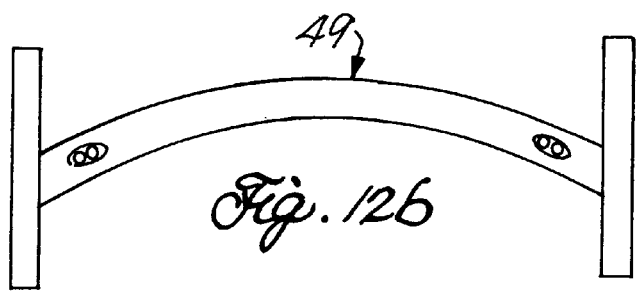
Figure 13A:
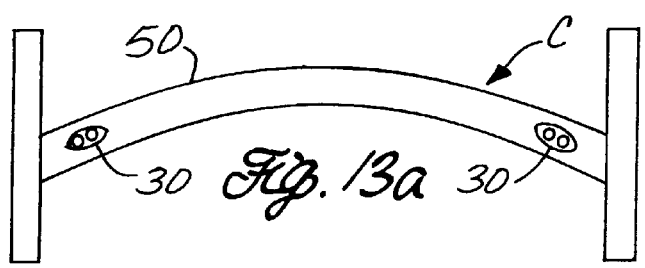
FIGS. 13(a) and 13(b) show cross-sectional views of the cornea and ring before and after a suture is removed therefrom.
Figure 13B:
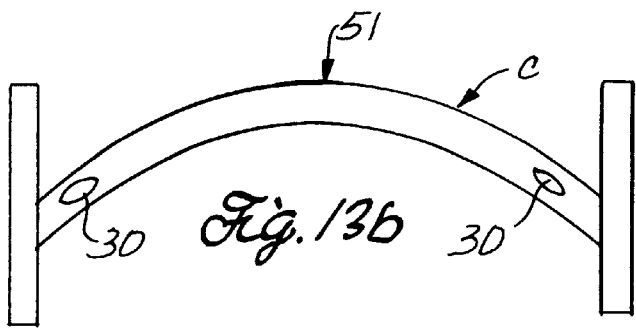

3. Post-operative adjustments. Simple, easily performed postoperative adjustments, which avoid the complications of reoperation concomitant with most keratorefractive procedures, are rendered feasible by this mechanism of adjustment. This postoperative adjustment can compensate for an inadequate preoperative ring choice, for corneal hydration intra-operatively which results in a different corneal curvature after corneal hydration status changes postoperatively, for an unexpected wound healing response in the periphery to the ring, and for later refractive changes caused by unknown factors. This postoperative adjustment is made possible by an elastic corneal ring containing suture which can be adjusted by suture cutting or lysis thus decreasing corneal curvature, suture removal thus decreasing ring thickness and increasing corneal curvature. Suture removal from the ring minimally disturbs the stroma-ring interface compared to removing the ring itself, thus minimizing the effects wound healing and edema will have on the adjustment. This postoperative adjustment appears to be a necessary adjunct to any method that seeks to meet the criteria for the ideal keratorefractive procedure. If the refractive outcome is not ideal, these are the steps that may be taken:

a. As demonstrated in FIGS. 12(a) and 12(b), if the corneal curvature is too steep and the patient is myopic, sutures tied at tension (38) may be cut thus is releasing some of the constricting ring of forces and thus flattening the corneal curvature (49). Ideally, the suture is cut near the knot, usually in the initial incision site. The suture may be cut with a sharp needle, knife, or even with a laser. If still inadequate, more than one suture strand may be cut. Although it is probably wise to leave at least one struture strand uncut, the two ends of the ring are unlikely to drift even if all the suture strands are cut. In the case that suture lysis results in excessive flattening, one of the cut strands may be completely removed from the ring and eye, resulting in a relative decrease in thickness of the ring with a concomitant steepening of the corneal curvature. If, in the unlikely event that a suture is difficult to remove, that suture may be cut at 180 degrees away and then each half removed through the initial incision.

b. As shown in FIGS. 13(a) and 13(b), if the corneal curvature 50 is too flat after surgery [FIG. 13(a)], sutures that have relatively little or no tension may be cut and removed, thus steepening the corneal curvature as shown in FIG. 13(b) with a myopic shift as described above. This is why it is essential that some of the sutures be tied with little or no tension at the initial surgery. If there is overcorrectior of the adjustment and removal of the suture material results in excessive steepening, a suture strand with tension may be cut and left in place, thus flattening the cornea.

Figure 14A:
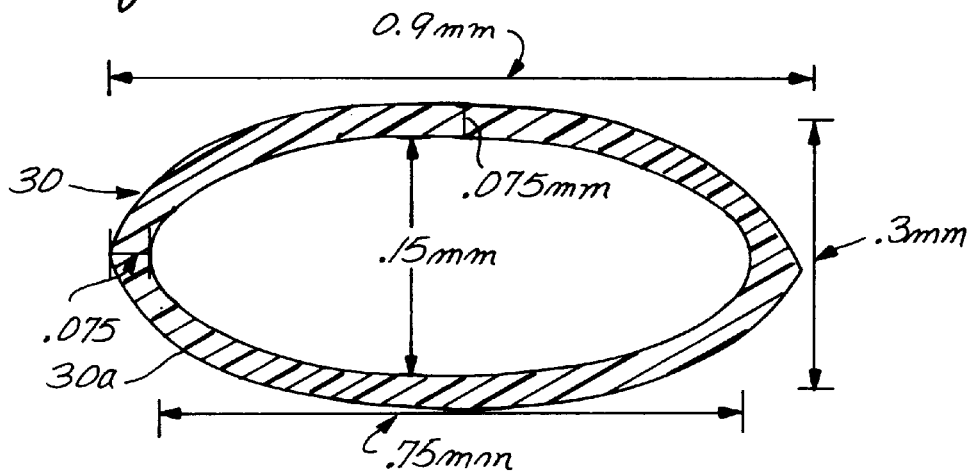
FIG. 14(a) is a radial cross-section of the ring of the invention and showing typical dimensions thereof.
Figure 14B:
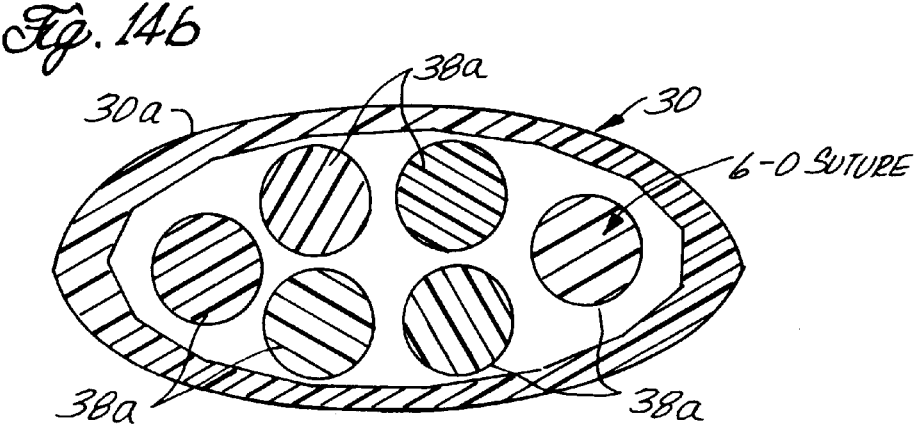
FIG. 14(b) is an enlarged radial cross section of the ring in FIG. 14(a) wherein the interior of the ring is filled with strands of suture material.
Figure 14C:
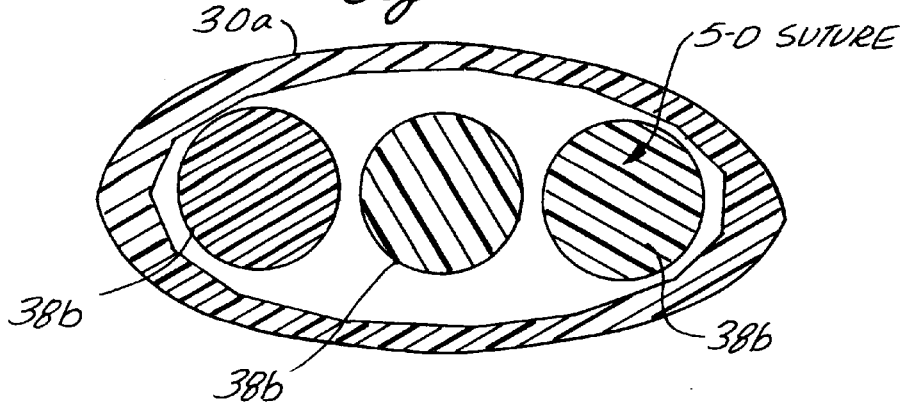
FIG. 14(c) is an enlarged radial cross section similar to FIG. 14(a) but showing the ring's interior filled with a lesser number of suture strands which are of greater diametrical thickness.

A typical adjustable ring 30 of the invention is shown in FIG. 14(a). The width of its outer diameter is 0.9 mm, overall thickness is 0.3 mm, and largest inner diameter is 0.75 mm and minor diameter is 0.15 mm. A ring of this size is expected to correct myopia by approximately 3 diopters. To calculate the number of suture strands which will comfortably fit. and the diopter change with removal of each strand, the following is assumed. The cross-sectional area of the oval-shaped ring is approximately 0.09 mm squared. Since this volume cannot be completely filled with suture—there are spaces between the round suture strands, the area that will be occupied by suture material is 78.5% ideally. Approximately three 5-0 suture strands 38b or five 6-0 suture strands 38a will fit into this space. Complete removal of all suture results in flattening by 0.15 mm or a 1.5 Diopter change. The average diopter change for each 5-0 suture removed from this typical embodiment is 0.5 diopter, for each 6-0 suture removed, 0.3 diopter change. Given an initial myopic patient, the outcome can be overshot by 50% of the initial refraction and the hyperopia still reasonably managed by suture removal alone.

Overtreatment resulting in hyperopia is a significant disadvantage in most keratorefractive procedures. In radial keratotomy the wound healing processes occur over a period of years and there is often a progressive hyperopia. Concerning photorefractive keratectomy, in one study, it was found the main reason patients did not have their second eye corrected with PRK (given that their first eye was corrected with PRK) was because of dissatisfaction with the hyperopia in their operated eye. The suture-ring technique easily corrects overcorrection hyperopia.

In a simple adaptation of the adjustable suture technique, this ring may be used to correct astigmatism. Curvature variation of the anterior surface of the cornea is responsible for the majority of cases of astigmatism. The light rays converge upon more than one plane and no one principal focus is formed. Astigmatism ordinarily depends on the presence of toroidal instead of spherical curvatures of the refractory surfaces of the eye. It thus becomes obvious that to correct astigmatism certain areas of the cornea must necessarily be corrected to a greater degree than other areas. A suture-filled ring can be varied in thickness along the circumference of the ring with the sections of the ring having increased thickness corresponding to the areas of the cornea having a steeper slope and requiring greater correction.

In the illustration of FIG. 15(a), the suture strand 32 completes almost 360 degrees within the ring. Another suture (33) is shorter and is absent at approximately 4–6 o'clock in the drawing. The suture (34) is the mirror image placement of (33), and is absent at 6–8 O'clock. Suture (35) folds over itself twice in the area of increased thickness. Suture (36) is the mirror image placement of (35). The end of the suture (37) is attached to the ring by glue or other means. The end of the suture on the other side (38) is likewise fixed. As illustrated by the greater thickness of the cross section of the ring in FIG. 15(b) as compared to the size of the crossection in FIG. 15(c), the areas with more suture have augmented thickness by up to 50% and thus allow for the differential correction required in astigmatic conditions.

If the astigmatism is overcorrected, suture strands (35) and (36) may be pulled until the loop (31) is removed and then cut at the point where the suture emerges from the ring. The removal of the loop (31) reduces the ratio of the thick area to thin area of the ring from ⅔ to ⅓. In the event that the astigmatism is undercorrected, suture (32) may be completely removed, increasing the ratio from ⅔ to ½.

Many different variations on this theme are possible, with some examples shown in FIGS. 16(a), 16(b) and 16(c). The suture strands 38a–38c as shown in FIG. 16(a), 38(d)–38(g) in FIG. 16(b), and 38(h)–38(k) in FIG. 16(c) can be varied by the number, length, diameter, presence of one or more loops at the end of a strand, and whether or not the suture strand is fixed to the ring. The variations can occur in the elastic ring which may have a supporting backbone of PMMA or other polymeric material. The thickness of the ring's shell may also be varied. The head and tail of the ring are brought into place and fixed. All the sutures are not necessarily tied. Suture adjustment is based on principles previously discussed. The manipulation of suture strands is usually through the initial insertion site, however, the ring may have a small circle removed from the anterior shell, to provide a small hole 90 as seen in FIG. 7(a) and located 180 degrees away from the original incision site, through which suture strands may be adjusted or removed. The strands are not necessarily 360 degrees in length as seen in FIGS. 15 and 16 and they may also be cut at their mid-length so as to facilitate suture removal at a later date.

In another embodiment, the ring may have areas of increased thickness formed by the presence of a flexible, curved, transparent material 71 that is inserted into the hollow ring shell 30(a) and that may be composed of the same material as the ring wall or a stiffer substance such as PMMA (refer to FIG. 17).

This curved rod 71 may have various transverse cross-section shapes, preferably conforming to that of the ring cross-section and more than one rod 71 may be provided. It may be 10 to 360 degrees in chord length. The ends 71a of the curved rods are gradually tapered so that the thickness at the rod ends approximates the thinnest areas of the ring. The thickness of the curved rod can be varied so that the thick section 76 of the ring may be several times the thickness of the thinnest sections 75 of the ring. 120 to 180 degrees away at the opposite side of the ring, there is a similar curved rod 71 that may be similar in length and thickness, but not necessarily so. The two curved rods are connected to each other by suture strands S as demonstrated in FIG. 17(a). The axis of astigmatism may be adjusted at a later date through the initial incision site by pulling the suture strand in one direction or the other, thus changing the position of the curved rods within the ring chamber and with respect to their direction from the central axis of the ring. An individual curved rod may have a suture that connects one end to the other such that each curved rod can be adjusted independently. As previously stated, many different variations on this theme are possible. This particular subembodiment may be used with any of the previous processes described.

An important advantage of this design is the ease of reversibility of the procedure. The procedure may be completely reversed by the surgical removal of the device or the refractive effect may be partially altered as previously described. The adjustments themselves may be reversed.

Figure 18A:
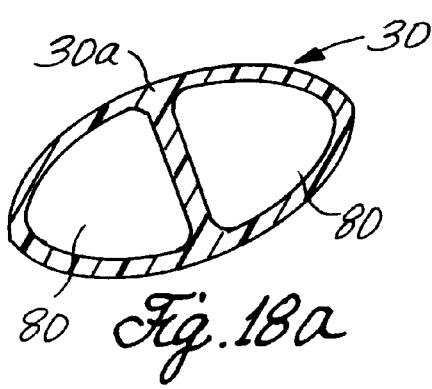
FIGS. 18(a)–18(c) each show a transverse radial cross-sectional view of the modified forms of the ring of the invention showing variations in ring design.
Figure 18B:
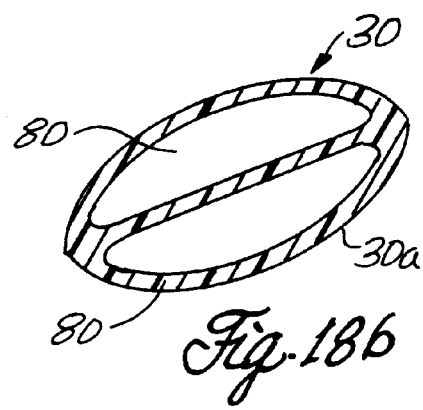
Figure 18D:
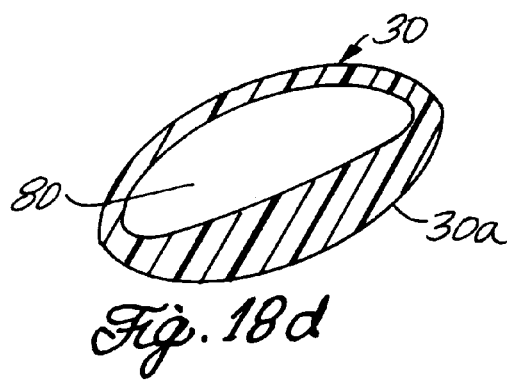
FIG. 18(d) is a plan view of another form of the adjusting ring of the invention and showing the locations of isolated compartments therein.
Figure 18C:
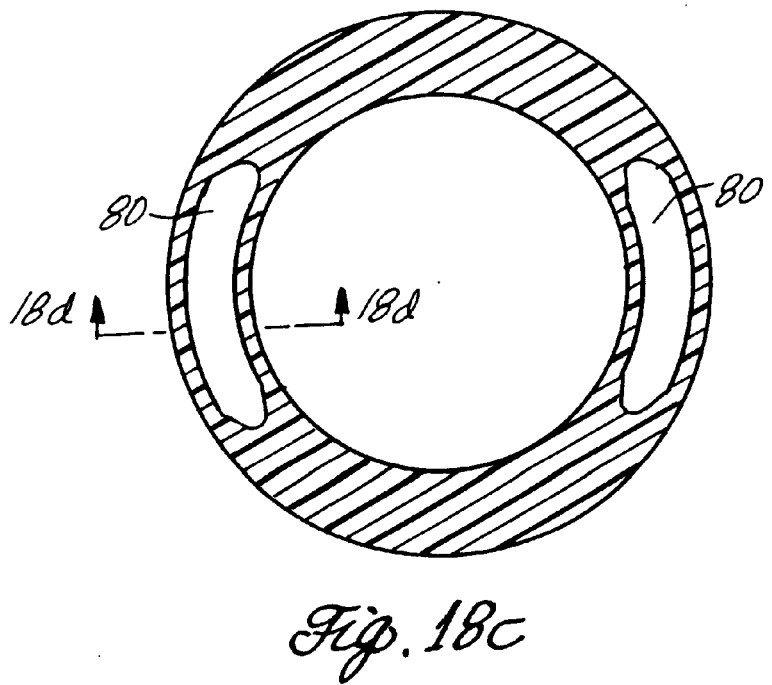

In yet another embodiment of the adjustable ring, there are present one or more compartments 80 within the ring, each water-tight and filled with a biocompatible fluid such as saline or a biocompatible gel. Each chamber is distinct and separate from the other chambers. Referring to FIGS. 18(a) and 18(b) which depict a cross-section of the ring 30, the chambers 80 can vary in number, shape, size, and may extend 360 degrees or may only extend partly around the ring. The shell 30(a) of the ring is similar to that previously described for the suture-filled ring. The properties of the shell previously described apply for this ring also.

The previous principles of adjusting corneal curvature with the various other ring designs also apply to this embodiment. In this design, the ring thickness is decreased by selectively puncturing a compartment, allowing fluid to leak out, or the fluid may be removed with a syringe and needle. More than one compartment may be punctured as necessary. When correcting myopia, a hyperopic outcome is very difficult to correct with any of the current keratorefractive procedures and overcorrection of myopia does occur. With this design, a hyperopic outcome is relatively easily reversed by fluid removal through selective puncture of one or more compartments. Simple deflation of the ring by fluid removal from one or more compartments results in decreased ring thickness, thus allowing fine-tuning of the refractive outcome.

Inasmuch as astigmatism is corrected by altering the thickness of the ring as previously described, this ring is also well-suited in the correction of astigmatism by the presence of certain size and shape chambers which add dimension to appropriate areas of the ring, relative to the other areas. Selective puncturing of these chambers may modify the outcome in the correction of astigmatism.

Again, this sub-embodiment may also be used in combination with any of the previous processes described.

It is therefore to be appreciated that by use of the present invention, the disadvantages of traditional refractive surgery procedures are avoided, such as 1) progressive hyperopia with radial keratotomy. Hyperopia in any refractive procedure is a generally worse outcome because the patient does not have clear vision at any range and because hyperopia is much more difficult to correct. The described procedure is particularly well-suited to adjust a hyperopic refractive outcome. 2) Irreversibility of radial keratotomy and laser ablation surgeries. 3) Surgical manipulation of the central visual axis with the potential for scar and stromal haze formation following laser ablation procedures. 4) Regression with laser ablation procedures, especially following re-operation. 5) Reduction of positive sphericity with RK and laser ablation which may result in increased image aberration. 6) The possible need for repetitive explanting and implanting of ICR's, which may cause shearing of corneal peripheral channel lamellae with associated decrease in effect and also scar formation.

Most refractive surgery procedures use nomograms to calculate the correction required and cannot completely account for an individual's variable response to refractive surgery. Oftentimes, an enhancement procedure with all its unpredictability is relied upon to correct the residual refractive error, with its concomitant increase in complication rate and scar formation. This new espoused device allows for the fact that individual tissue response to the calculated correction may not be completely predictable, and permits easy adjustments at the time of surgery and more importantly, at a later date after corneal hydration and would healing responses have stabilized, by simple suture cutting or removal. The nature of these adjustments minimally disturb the ring-corneal interface and is thus expected to have a much more predictable effect than even the implantation of the ring itself which causes less of a wound healing response than current procedures such as RK and PRK. In addition, when correcting myopia, a hyperopic outcome is very difficult to correct with any of the current keratorefractive procedures and overcorrection of myopia does occur. In this invention, a hyperopic outcome is relatively easily reversed by suture removal.

Typically, in most keratorefractive procedures for myopia, the surgeon aims for slight undercorrection because of the wish to avoid a hyperopic outcome. The ease with which a hyperopic outcome is adjusted with the ring of the present invention enables the surgeon to aim for full correction, thereby obtaining the full benefit of the nomogram, and resulting in a higher percentage of patients with the desired refractive outcome even without an adjustment of the ring. The surgeon may even choose to slightly overcorrect followed by an is adjustment.

The essence of this invention lies in the assumption that individual responses to any keratorefractive surgical procedures are variable and that a simple, safe, and effective technique for corneal curvature adjustment is necessary and that this adjustment should minimally disturb surrounding tissue thus allowing for a predictable effect. It should also be easily accomplished at some post-operative date after implantation of the ring and after factors affecting corneal curvature changes have stabilized. A key feature of this invention lies in the ability of the ring in its various embodiments to be adjusted in thickness and/or circumference with ease at the time of implantation but more importantly on multiple occasions thereafter by simple suture cutting or removal of biocompatible filler material, thus allowing fine-tuning of the refractive outcome.

In conclusion, in correcting refractive errors with the adjustable ring technique, the feeling of finality does not set in even with an initial inaccurate correction, with inadequate adjustment, or even when the last suture is cut and the last suture removed, or the last chamber drained, because the ring itself can be easily removed or better yet, left in place while other refractive procedures, such as laser ablation surgery are considered, if that point is ever reached.

It is also to be appreciated that the foregoing description of the invention has been presented for purposes of illustrations and explanation and is not intended to limit the invention to the precise form of apparatus and manner of practice herein. It is to be appreciated therefore, that changes may be made by those skilled in the art without departing from the spirit of the invention.

I claim as my invention:

1. A process for altering a corneal curvature of an eye, comprising:

forming a circular channel in the cornea beneath the corneal surface; and inserting a corneal ring with an adjustable thickness into the circular channel, the ring being comprised of an annular hollow collapsible member containing solid removable filler material, wherein if it is necessary to further alter the corneal curvature after implantation of said corneal ring, the corneal curvature is altered by a process comprising:

making an incision into the anterior cornea at a point near the ring; and removing at least some of the solid filler material from within the collapsible member of the ring with minimal disturbance to the ring-corneal interface.

2. A process for altering a corneal curvature of an eye, comprising:

forming a circular channel in the cornea beneath the corneal surface; and inserting a corneal ring with an adjustable thickness into the circular channel, the ring being comprised of an annular hollow collapsible member containing solid removable filler material, wherein adjusting the ring thickness further comprises moving at least some of the solid material within the implanted collapsible member causing a change in thickness of the hollow member along at least part of its circumference, thus adjusting the corneal curvature; and removing at least some of the solid material from the implanted collapsible member causing at least partial collapse of the hollow member along at least part of its circumference, thus steepening the corneal curvature.

3. A process for altering a corneal curvature of an eye, comprising:

forming a circular channel in the cornea beneath the corneal surface;

inserting a corneal ring with an adjustable thickness into the circular channel, the ring being comprised of an annular hollow collapsible member containing solid removable filler material, wherein adjusting the ring thickness further comprises moving at least some of the solid material within the implanted collapsible member causing a change in thickness of the hollow member along at least part of its circumference, thus adjusting the corneal curvature; and removing at least some of the solid material from the collapsible member, without moving the collapsible member about the central axis of the ring, thus steepening the corneal curvature.

4. A process for altering a corneal curvature of an eye, comprising:

forming a circular channel in the cornea beneath the corneal surface; and inserting a corneal ring with an adjustable thickness into the circular channel, the ring being comprised of an annular hollow collapsible member containing solid removable filler material, wherein said solid removable filler material is biocompatible and is comprised of one or more strands.

5. The process of claim 4 wherein the solid material is comprised of at least one strand of material extending along at least a portion of the ring.

6. A corneal ring having an adjustable thickness for altering a corneal curvature of an eye, the corneal ring comprising an annular hollow collapsible member containing solid removable filler material wherein the solid removable material is biocompatible and is comprised of one or more strands.

7. A corneal ring having an adjustable thickness for altering a corneal curvature of an eye, the corneal ring comprising an annular hollow collapsible member containing solid removable filler material wherein the solid removable material is biocompatible and comprises at least one strand of material extending along at least a portion of the ring.

* * * * *